United States Patent [19]
Wilson et al.

[11] Patent Number: 5,133,207
[45] Date of Patent: Jul. 28, 1992

[54] APPARATUS AND METHOD FOR SIMULTANEOUSLY TESTING THE PERMEABILITY OF MULTIPLE CORE SPECIMENS

[75] Inventors: Logan D. Wilson, Alvin; Edwin E. Glazier, Jewett; Charles J. Kelly, Buffalo, all of Tex.

[73] Assignee: Houston Industries Incorporated, Houston, Tex.

[21] Appl. No.: 655,064

[22] Filed: Feb. 14, 1991

[51] Int. Cl.⁵ .......................................... G01N 15/08
[52] U.S. Cl. .................................................. 73/38
[58] Field of Search ........................................ 73/38

[56] References Cited

U.S. PATENT DOCUMENTS

| | | | |
|---|---|---|---|
| 966,078 | 10/1910 | Bowman | 73/38 |
| 2,788,657 | 9/1957 | Innes | 73/38 |
| 3,018,660 | 1/1962 | Schmid | 73/38 X |
| 3,850,040 | 12/1974 | Orr, Jr. et al. | 73/38 X |
| 4,043,407 | 8/1977 | Wilkins . | |
| 4,300,386 | 11/1981 | Gupta | 73/38 |
| 4,304,122 | 12/1981 | Tentor | 73/38 |
| 4,384,474 | 5/1983 | Kowalski | 73/38 |
| 4,468,951 | 9/1984 | Garcia et al. | 73/38 |
| 4,515,007 | 5/1985 | Herman | 73/38 |
| 4,566,326 | 1/1986 | Lowell | 73/38 X |
| 4,573,342 | 3/1986 | Jones | 73/38 |
| 4,791,822 | 12/1988 | Penny | 73/865.6 |

FOREIGN PATENT DOCUMENTS

| | | | |
|---|---|---|---|
| 245436 | 10/1969 | U.S.S.R. | 73/38 |
| 430311 | 5/1975 | U.S.S.R. | 73/38 |

*Primary Examiner*—Hezron E. Williams
*Assistant Examiner*—Joseph W. Roskos
*Attorney, Agent, or Firm*—Pravel, Gambrell, Hewitt, Kimball & Krieger

[57] ABSTRACT

An apparatus and method for simultaneously testing the permeability of a plurality of core specimens is disclosed. The apparatus includes a reservoir to contain a fluid and a plurality of permeameters in fluid communication with the reservoir. The apparatus also includes valves for individually controlling the supply of fluid to the permeameters and a buret and flask for measuring the amount of fluid passing individually through each core specimen in each permeameter. The apparatus also includes a pressurized gas source for pressurizing the fluid in the reservoir with gas and a pressure regulator to allow multiple permeability tests to be conducted simultaneously but at a different pressure than other concurrent permeability tests.

23 Claims, 3 Drawing Sheets

APPARATUS AND METHOD FOR SIMULTANEOUSLY TESTING THE PERMEABILITY OF MULTIPLE CORE SPECIMENS

BACKGROUND OF THE INVENTION

1. Field of the Invention

The present invention relates to a method and apparatus for ascertaining the permeability of core specimens, and more particularly to a method and apparatus for simultaneously testing multiple core specimens.

2. Description of the Related Art

The permeability of a material, such as soil or rock, is a very important parameter to a foundation engineer. A material is said to be permeable if it contains continuous voids. All soils and rocks are permeable; however, there are vast differences in the degree of permeability of various earth materials. The measurement of permeability of a soil or rock indicates how fast a fluid will flow through the given material.

Depending on the type of soil that is being tested, a permeability test may last as long as several days and even a few weeks. Prior art permeability testing devices are capable of performing only one permeability test on one core specimen at a time. Permeability tests often need to be performed on several core specimens in a relatively short period of time. Due to the fact that each test may last several days, either several permeability testers must be utilized or a prolonged period of time is required to test all of the soil specimens.

In U.S. Pat. No. 4,573,342 to Jones, a permeability testing apparatus including a carousel capable of carrying a plurality of core specimens is disclosed. The apparatus automatically determines the permeability for a plurality of core specimens; however, only one specimen is tested at a time. When the test on one core specimen is completed, the apparatus automatically rotates the carousel to the next core specimen until all of the core specimens have been individually tested. This apparatus affords little, if any, time saving over sequentially testing individual specimens in a sequence.

It would be desirable to have a permeability testing device capable of simultaneously testing multiple core specimens. It would also be desirable to be able to start and/or finish the permeability test on a core specimen independently of other ongoing permeability tests. It would further be desirable to be able to conduct simultaneous permeability tests on a plurality of core specimens at more than a single pressure.

SUMMARY OF THE INVENTION

The present invention provides a new and improved permeability testing apparatus which is capable of performing permeability tests simultaneously and concurrently on multiple core specimens. One or more tests can be started or finished independently of other ongoing tests. The present invention further includes the ability to conduct simultaneous permeability tests at more than a single pressure.

DETAILED DESCRIPTION OF THE INVENTION

Figure 1:
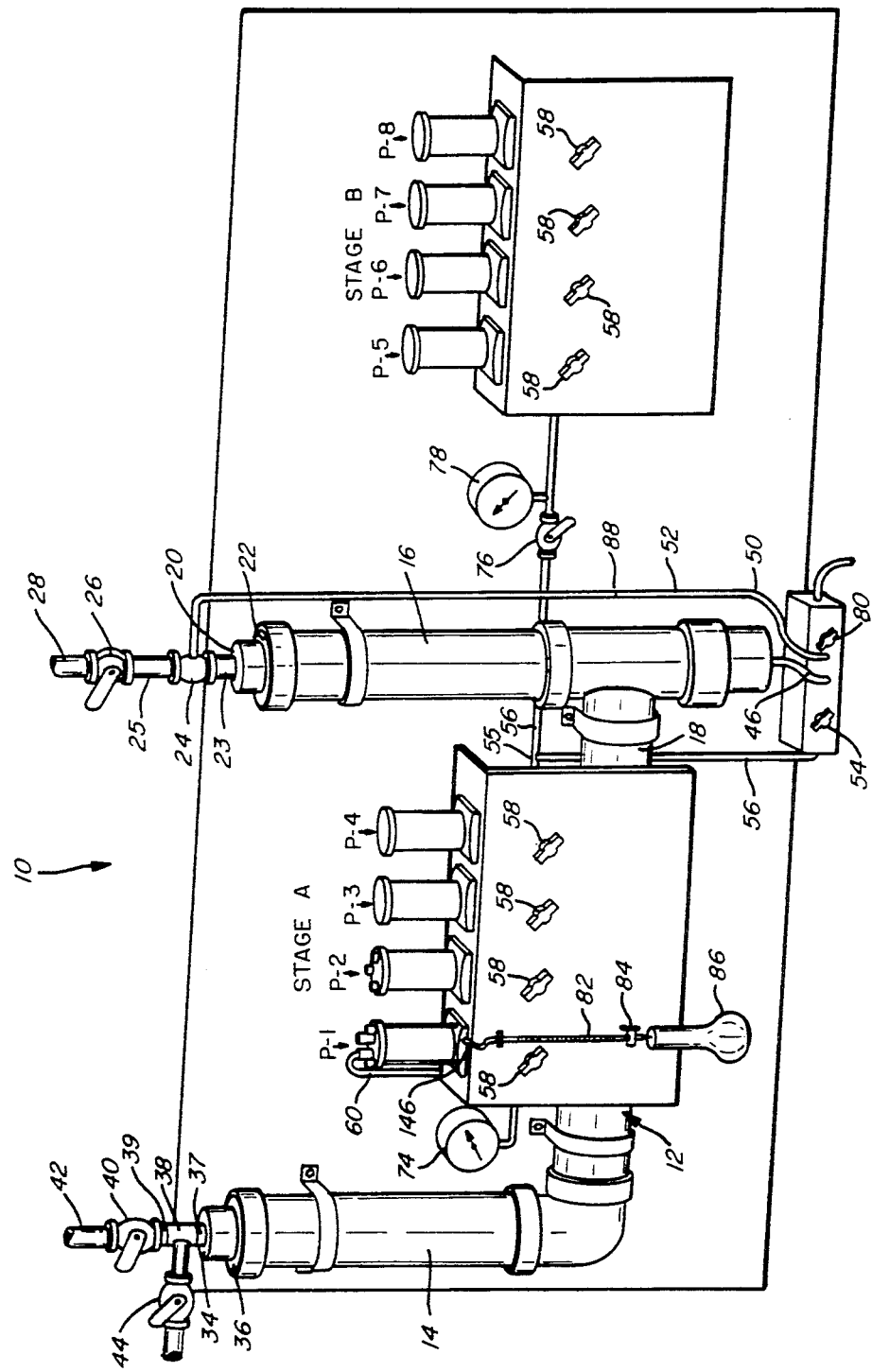
FIG. 1 is an isomeric view of a preferred embodiment of a permeability testing apparatus according to the present invention.

In the drawings, an apparatus 10 according to the present invention for simultaneously testing the permeability of multiple core specimens is shown. The apparatus 10 includes a reservoir 12 for holding a fluid 13, such as water, and gas pressure, typically air pressure. The reservoir 12 is made from hollow tubing or piping and is generally U-shaped, having a left vertical tubular member 14 and a right vertical tubular member 16 joined together by a horizontal tubular member 18. The reservoir 12 may be made from various suitable piping materials, including polyvinyl chloride (PVC) pipe.

The right vertical tubular member 16 has a fluid inlet port 20 positioned at an upper end 22 of the right vertical tubular member 16. The fluid inlet port 20 is threadably engaged with a short pipe nipple 23 to a pipe tee 24. The pipe tee 24 is oriented so that the through bore of the pipe tee 24 is vertically oriented and the cross bore is horizontally oriented. The lower end of the through bore of the pipe tee 24 is threadably engaged with the fluid inlet port 20 via the short pipe nipple 23. The upper end of the through bore of the pipe tee 24 is threadably engaged with a fluid shutoff valve 26 via a second pipe nipple 25. A fluid supply line 28 connects a fluid source (not shown) with the fluid shutoff valve 26. Thus, by opening fluid shutoff valve 26, the fluid 13 is permitted to enter the reservoir 12.

The left vertical tubular member 14 of the reservoir 12 includes a gas inlet port 34 located at an upper end 36 of the left vertical tubular member 14. A pipe tee 38 having a vertically oriented through bore is threadably connected to the gas inlet port 34 via a short pipe nipple 37. The upper end of the through bore of the pipe tee 38 is connected to a gas shutoff valve 40 via a second short pipe nipple 39. A gas supply line 42 connects a pressurized gas source (not shown) to the gas shutoff valve 40. Thus, when the gas shutoff valve 40 is opened, pressurized gas or air is allowed to enter the reservoir 12. The cross bore opening of the pipe tee 38 is connected to a vent valve 44 for venting excessive gas pressure in the reservoir 12 to the atmosphere.

A fluid outlet port 30 is located at a lower end 32 of the right vertical tubular member 16. An inlet tubing 46 connects the fluid outlet port 30 of the reservoir 12 to a manifold 48. The fluid 13 in the reservoir 12 is in fluid communication with the manifold 48. The manifold 48 branches into three outlets. A tubing 50 having a sight glass 52 for viewing and monitoring the elevation of the fluid 13 in the reservoir 12 is connected between one outlet of the manifold 48 and the cross bore of the pipe tee 24 at the upper end 22 of the right vertical member 6. A second outlet of the manifold 48 is connected to a drain valve 80. The drain valve 80 is opened to drain the fluid 13 from the reservoir 12. A third outlet of the manifold 48 is connected to a main isolation valve 54. The main isolation valve 54 connects a feed line 56 to a plurality of permeameter isolation valves 58.

Figure 2:
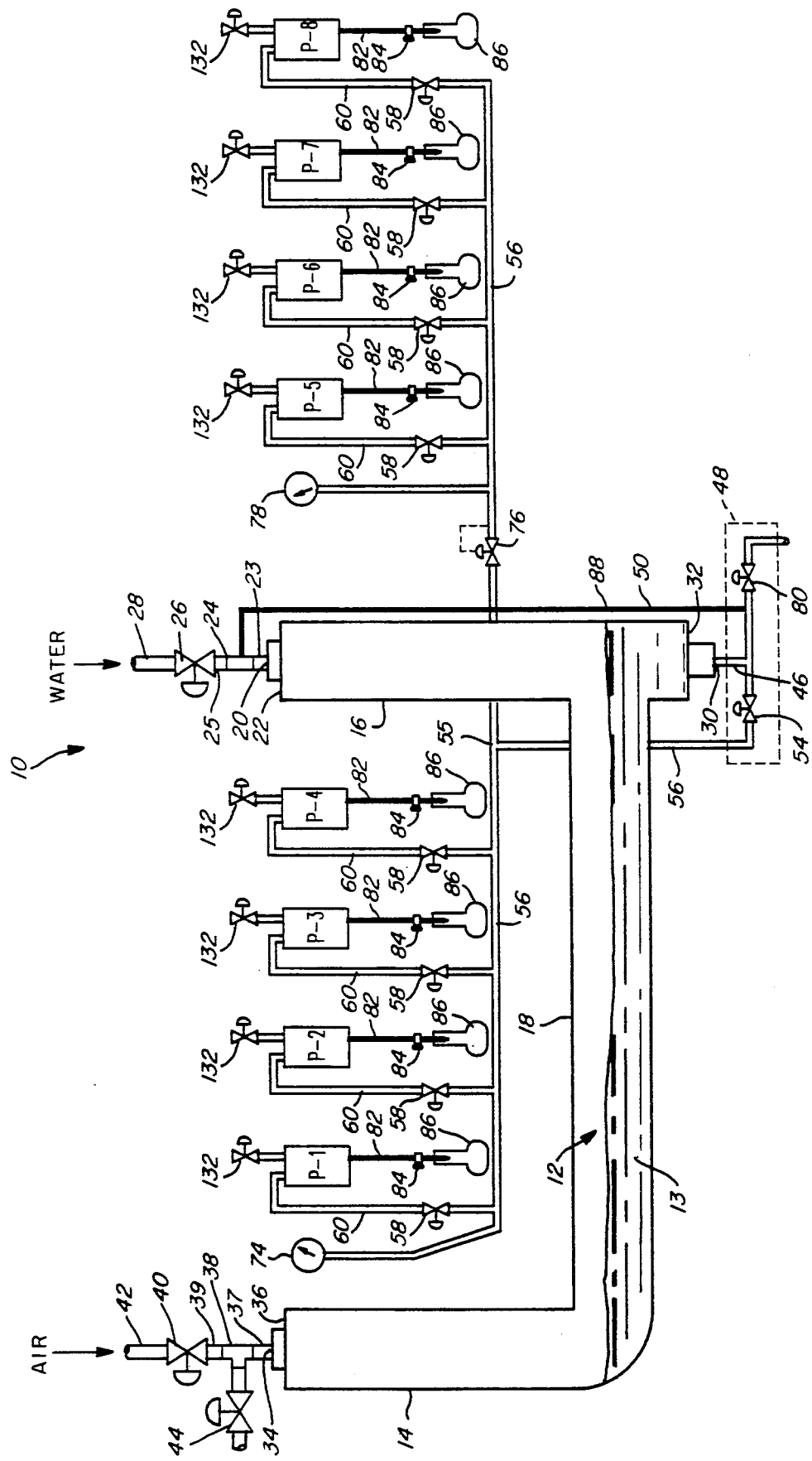
FIG. 2 is a schematic operating diagram illustrating the permeability testing apparatus of FIG. 1.

In the preferred embodiment, as shown in FIGS. 1 and 2, a plurality of permeameters, referred to generally as P, have been individually identified as P-1 through P-8, respectively. The eight permeameters have been divided into two stages, a Stage A and a Stage B. Stage A includes permeameters P-1, P-2, P-3 and P-4, while Stage B includes permeameters P-5, P-6, P-7 and P-8.

Since the fluid connections to each of the permeameters are of like construction, like structure performing like functions bear like reference numerals. A plurality of supply lines 60 connect the permeameter isolation valves 58 to the permeameters P-1, P-2, P-3, P-4, P-5, P-6, P-7 and P-8. A Stage A pressure gauge 74 is connected to the feed line 56 to monitor the pressure of the fluid 13 in the feed line 56 which supplies permeameters P-1, P-2, P-3 and P-4 in Stage A.

As illustrated in FIGS. 1 and 2, the feed line 56 from the main isolation valve 54 has a tee 55 for branching to Stage A and Stage B. The branch of the feed line 56 which feeds Stage B includes a pressure regulator 76 for regulating the pressure of the fluid 13 in the feed line 56 which supplies permeameters P-5, P-6, P-7 and P-8 in Stage B. Stage B also has a pressure gauge 78 for monitoring the pressure of the fluid 13 in the feed line 56 which supplies permeameters P-5, P-6, P-7 and P-8 in Stage B.

Figure 3:
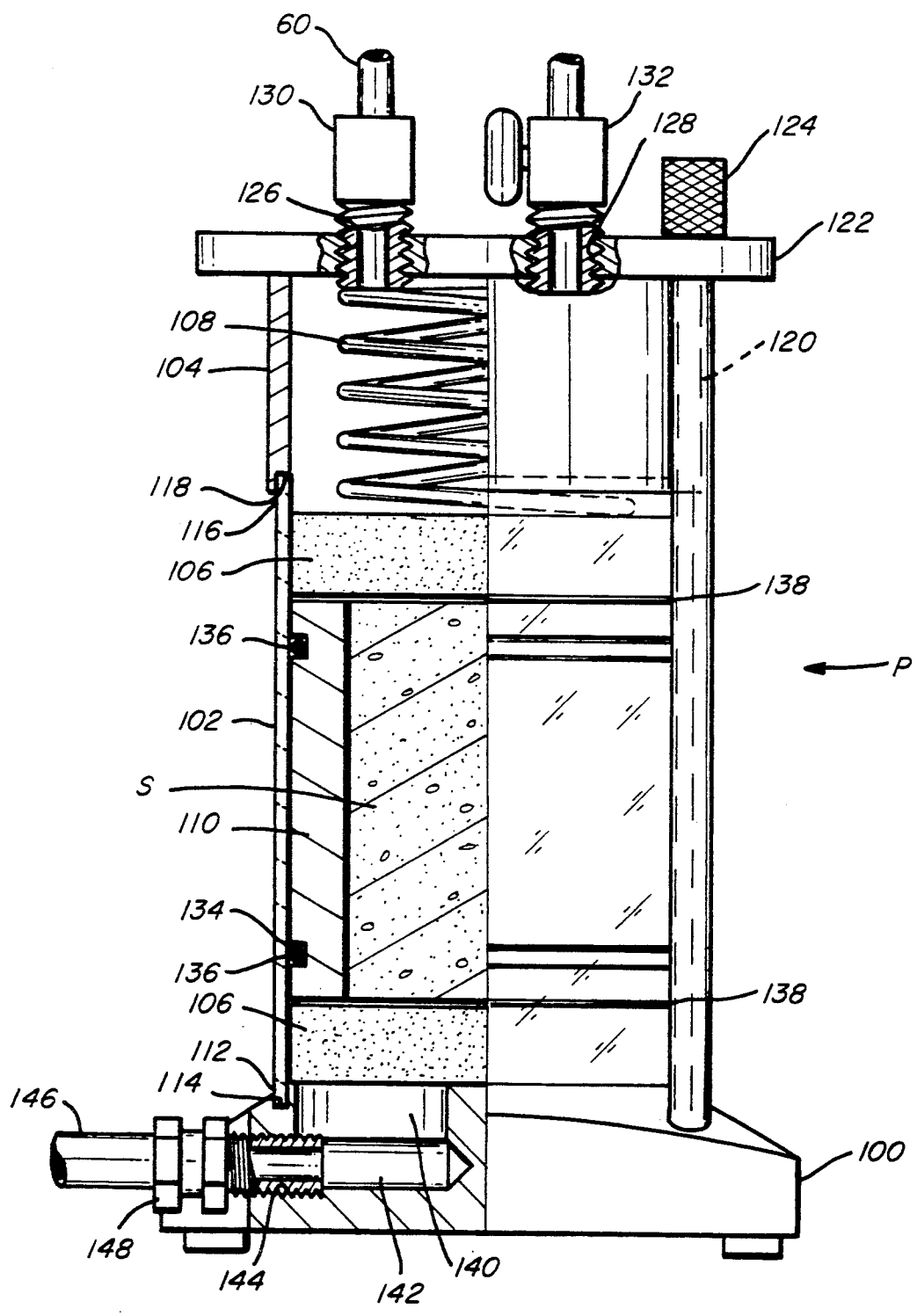
FIG. 3 is an elevation view, taken partly in cross-section, of a permeameter of the permeability testing apparatus of FIG. 1.

Each of the permeameters P is of like construction and thus like components bear like reference numerals. Referring now to FIG. 3, each of the permeameters P includes a base 100, a cylinder 102, a cap 104, a pair of porous stones 106, a compression spring 108 and a specimen mold 110 which contains a test soil specimen S. The cylinder 102, typically made out of plexiglass, has a lower end 112 which rests in a receiving groove 114 formed in the base 100. An upper end 116 of the cylinder 102 similarly rests in a recessed portion 118 of the cap 104. The cap 104, cylinder 102 and base 100 are held together by a plurality of rods 120 circumferentially spaced around the perimeter of the cylinder 102. The rods 120 have threaded ends (not shown) which engage threaded recesses (not shown) in the base 100 at the lower end and which extend through a cap plate 122 at the upper end. The upper end of the rod 120 is engaged with a nut 124 which firmly secures the cap 104, the cylinder 102 and the base 100.

The cap plate 122 further includes a threaded fluid inlet 126 and a threaded air release outlet 128. The threaded fluid inlet 126 engages a threaded fitting 130 of the supply line 60. The threaded air release outlet 128 receives a threaded end of an air release valve 132.

The specimen mold 110 includes a pair of exterior recessed grooves 134 for receiving sealing rings 136 to seal off the annulus between the inside diameter of the cylinder 102 and the outside diameter of the specimen mold 110.

The porous stones 106 are positioned both above and below the specimen mold 110. A filter paper 138 may be placed between each porous stone 106 and the specimen mold 110. The lower porous stone 106 is placed on the base 100 of the permeameter P. The compression spring 108 is positioned between the cap plate 122 and the upper porous stone 106 to prevent expansion of the specimen S during the permeability test.

The base 100 includes a cavity 140 for receiving the fluid 13 which passes through the porous stones 106 and the specimen S. The cavity 140 directs the fluid 13 to a channel 142 having an internally threaded opening 144. A short tubing 146 having a threaded fitting 148 engages the internally threaded opening 144 of the channel 142.

The short tubing 146 empties into a buret 82. The buret 82 is a graduated glass tube with a small aperture and stopcock 84 for measuring the amount of fluid 13 discharged from the permeameter P. When draining the buret 82 by opening the stopcock 84, a flask 86 is positioned beneath the buret 82.

OPERATION OF THE PRESENT INVENTION

Prior to beginning a permeability test with no other permeability test in progress, the reservoir 12 must be "charged." The reservoir 12 is charged with the fluid 13, preferably distilled, dyed water, through the water shutoff valve 26 while venting air through the vent valve 44. The reservoir 12 is charged to a "fill level" mark 88 on the sight glass 52. The water shutoff valve 26 and the vent valve 44 are then closed. A pressurized gas source (not shown) slowly pressurizes the reservoir 12 by opening the gas shutoff valve 40 until the desired pressure is obtained. The gas shutoff valve 40 is closed upon reaching the desired pressure in the reservoir 12. The main isolation valve 54 is slowly opened to fill the feed line 56 up to the permeameter isolation valves 58 of Stage A. Each of the permeameter isolation valves 58 in Stage A is slowly opened, one at a time, allowing the fluid 13 to purge any entrapped air in the feed line 56 and the supply line 60 via the air release valve 132. The permeameter isolation valves 58 in Stage A are then closed.

If more than four permeability tests are required, the pressure regulator 76 should be adjusted to the desired pressure and permeameter isolation valves 58 in Stage B are slowly opened, one at a time, to ensure that all entrapped air is purged from the feed line 56 to them.

It is important to note that the pressure regulator 76 regulates the pressure of the fluid 13 in Stage B. The pressure of the fluid 13 in Stage B can be no greater than the pressure of the fluid 13 in Stage A. When the pressure regulator 76 is fully open, the pressure of the fluid 13 in Stage B will equal the pressure of the fluid 13 in Stage A.

The test pressure desired depends on the type of material being tested. For example, a highly impermeable material will be tested at a higher pressure than a highly permeable material to effectively minimize the duration of the test. However, the same pressure, if applied to a highly permeable material, will result in a "blow out," resulting in inaccurate results. As shown in FIGS. 1 and 2, Stage A will be at one pressure and Stage B will be at the same or a lesser pressure. The pressure at each permeameter in a stage will be the same. Thus, when permeability tests are simultaneously in progress in permeameters P-1, P-2, P-3 and P-4, the pressure at permeameter P-1 will equal the pressure at permeameter P-2, which will equal the pressure at permeameter P-3, which will equal the pressure at permeameter P-4. Similarly, when permeability tests are simultaneously in progress in Stage B, the pressure at permeameters P-5, P-6, P-7, and P-8 will all be the same.

The core soil specimen S is placed in the specimen mold 110 according to conventional methods well known in the art. Both ends of the specimen S are trimmed flush with both the upper and lower face of the specimen mold 110. With the specimen S in place in the specimen mold 110, the filter paper 138 and porous stone 106 are arranged on both the upper and lower face of the specimen mold 110. A thin coating of petrolatum or petroleum jelly is applied to the sealing rings 136 to ensure a proper seal. This completed mold assembly is placed into the cylinder 102 with the lower porous stone 106 flush with the bottom of the cylinder 102.

The loaded cylinders 102 are then placed on top of the permeameter bases 100. The compression spring 108 is installed on top of the upper porous stone 106 and the cap 104 is then placed over rods 120. The cap 104 is secured by tightening the nuts 124 which seals the interfaces of the cap 104 to the cylinder 102 and the cylinder 102 to the base 103.

The apparatus 10 is then inspected for air bubbles remaining in the system and for any air or fluid leaks. Any air bubbles, if present, are removed and any air or fluid leaks are repaired. The fluid level in the reservoir 12 is adjusted, if needed, by adding fluid 13 through the fluid shutoff valve 26 or by draining excess fluid through the drain valve 80. The test pressure can be adjusted by pressurizing through the gas shutoff valve 40 or by venting excess pressure through the vent valve 44.

Once the desired test pressure has been obtained, the gas shutoff valve 40 and vent valve 44 are closed. The permeameter isolation valves 58 for the permeameters P in which tests are going to be conducted are then opened. The specimens S being tested become saturated. A constant test flow through the permeameters P into the burets 82 is established. A test flow may be defined as three equal, consecutive flow rate measurements. For example, a test flow may be defined as containing a minimum of one milliliter each over a given period of time. After test flow has been established, the buret 82 reading, time and temperature of the fluid 13 is recorded. The permeability test may be terminated after a certain volume of fluid 13 has passed through the specimen S into the buret 82.

Upon completion of a test, the permeameter isolation valve 58 may be closed and the permeameter P disassembled to remove the test specimen S. For example, if permeability tests are being performed in permeameters P-1, P-2 and P-5, and the test on the specimen S in permeameter P-1 is completed, the permeameter isolation valve 58 is closed and then permeameter P-1 may be disassembled and the test specimen S removed. This will not affect the ongoing tests in permeameters P-2 and P-5. Additionally, a new test specimen S may be placed in permeameter P-1 while tests are still ongoing in permeameters P-2 and P-5. Once the new test specimen S is installed in permeameter P-1, the permeameter isolation valve 58 may be opened and the test begun on the new test specimen S in permeameter P-1. As is evident from the above, the apparatus 10 of the present invention allows tests to be brought on or off line while simultaneously performing other tests through the use of the permeameter isolation valves 58 so that the other tests are undisturbed.

The description given herein is intended to illustrate the preferred embodiment of the present invention. It is possible for one skilled in the art to make various changes to the details of the apparatus and method without departing from the spirit of this invention. Therefore, it is intended that all such variations be included within the scope of the present invention as claimed.

I claim:

1. An apparatus for simultaneously testing the permeability of a plurality of core specimens, comprising:
    a reservoir to contain a fluid, said reservoir having a fluid inlet port and a fluid outlet port and including a substantially horizontal tubular member for containing the fluid;
    a plurality of permeameters with each said permeameter having a fluid inlet opening and a fluid outlet opening;
    means for supplying the fluid from said fluid outlet port of said reservoir to said fluid inlet opening of said plurality of permeameters;
    means for controlling the supply of fluid individually to each of said plurality of permeameters; and
    means for measuring the amount of fluid passing through the core specimen in each said permeameter.

2. The apparatus according to claim 1, wherein said means for supplying comprises:
    a feed line connecting said fluid outlet port of said reservoir to said fluid inlet opening of said plurality of permeameters.

3. The apparatus according to claim 2, wherein said means for controlling comprises:
    a main isolation valve placed between said reservoir and said feed line.

4. The apparatus according to claim 2, wherein said means for controlling comprises:
    a plurality of permeameter isolation valves placed in said feed line wherein each said permeameter isolation valve controls the supply of fluid to one said permeameter.

5. The apparatus according to claim 4, wherein each said permeameter isolation valve of said plurality of permeameter isolation valves includes a control so that each said permeameter isolation valve is controlled independently of the other said permeameter isolation valves to permit a permeability test in one of said plurality of permeameters to be independently started or finished irrespective of ongoing permeability tests in other said permeameters.

6. The apparatus according to claim 1, wherein said horizontal tubular member has first and second ends and said reservoir comprises:
    substantially vertical tubular members connected to said first end and said second end of said substantially horizontal tubular member.

7. The apparatus according to claim 1, further comprising:
    means for charging said reservoir with fluid.

8. The apparatus according to claim 7, wherein said means for charging comprises:
    a fluid source in fluid communication with said fluid inlet port of said reservoir to fill said reservoir to a given level; and
    a valve to control the amount of fluid allowed to enter said reservoir from said fluid source.

9. The apparatus according to claim 7, further comprising:
    means for pressurizing said reservoir; and
    said reservoir further including a gas inlet port.

10. The apparatus according to claim 9, wherein said means for pressurizing comprises:
    a pressurized gas source connected to said gas inlet port of said reservoir; and p1 a valve to control the flow or pressurized gas into said reservoir.

11. The apparatus according to claim 9, further comprising:
    a pressure gauge connected to said means for supplying the fluid for indicating the test pressure of the fluid being supplied to said plurality of permeameters.

12. An apparatus for simultaneously testing the permeability of a plurality of core specimens at a plurality of pressures, comprising:
   a reservoir to contain a fluid, said reservoir having a fluid inlet port, a gas inlet port, and a fluid outlet port;
   means for charging said reservoir with fluid;
   means for gas pressurizing said reservoir;
   a plurality of permeameters, each said permeameter having a fluid inlet opening and a fluid outlet opening;
   means for supplying the fluid from said fluid outlet port of said reservoir to said fluid inlet opening of each of said permeameters;
   means for controlling the supply of fluid to said plurality of permeameters; and
   means for separately measuring the amount of fluid passing through the core specimen in each said permeameter,
   wherein said plurality of permeameters are divided into a first group of permeameters and a second group of permeameters, and said means for supplying the fluid includes a first feed line providing fluid communication between said reservoir and each said permeameter in said first group of permeameters and further includes a second feed line providing fluid communication between said reservoir and each said permeameter in said second group of permeameters.

13. The apparatus according to claim 12, wherein said means for controlling comprises:
   a plurality of permeameter isolation valves placed in said first and second feed lines wherein each said permeameter isolation valve controls the supply of fluid to one said permeameter.

14. The apparatus according to claim 13, further comprising:
   means for regulating the pressure of the fluid in said second feed line.

15. The apparatus according to claim 14, wherein said means for regulating the pressure includes a pressure regulator placed in said second feed line.

16. The apparatus according to claim 15, wherein said pressure regulator regulates the pressure of the fluid supplied to each said permeameter in said second set of permeameters.

17. The apparatus according to claim 16, wherein each said permeameter isolation valve of said plurality of permeameter isolation valves includes a control so that each said permeameter isolation valve is controlled independently of the other said permeameter isolation valves to permit a permeability test in one of said plurality of permeameters to be independently started or finished irrespective of ongoing permeameter tests in other said permeameters.

18. The apparatus according to claim 12, further comprising:
   means for regulating the pressure of the fluid in said second feed line.

19. The apparatus according to claim 18, wherein said means for regulating the pressure includes a pressure regulator placed in said second feed line.

20. The apparatus according to claim 19, wherein said pressure regulator regulates the pressure of the fluid supplied to each said permeameter in said second set of permeameters.

21. A method for simultaneously testing the permeability of a plurality of core specimens at a plurality of pressures, comprising the steps of:
   charging a reservoir with fluid;
   pressurizing the reservoir with gas;
   filling a feed line with fluid between the reservoir and a first set of permeameters and between the reservoir and a second set of permeameters;
   purging any entrapped gas in the feed line between the reservoir and the first and second sets of permeameters;
   placing a core specimen in each permeameter in which a permeability test will be conducted;
   adjusting a pressure regulator to control the pressure of the fluid being supplied to the second set of permeameters;
   opening a permeameter isolation valve for each permeameter in which a permeability test will be conducted;
   performing the permeability test on each core specimen independently of the other core specimens being tested;
   closing the permeameter isolation valve for the permeameter in which the permeability test is completed; and
   removing the core specimen from the permeameter in which the permeability test is completed independently of the other core specimens being tested.

22. The method according to claim 21, further comprising the steps of:
   placing another core specimen in a permeameter while a permeability test is being conducted in a different permeameter; and
   opening the permeameter isolation valve for the permeameter in which said another core specimen has been placed; and
   performing the permeability test on said another core specimen independently of the other core specimens being tested.

23. An apparatus for simultaneously testing the permeability of a plurality of core specimens and permitting a permeability test on individual core specimens to be started or finished irrespective of ongoing permeability tests on other core specimens, the apparatus comprising:
   a reservoir to contain a fluid, said reservoir having a fluid inlet port and a fluid outlet port;
   a plurality of permeameters with each said permeameter having a fluid inlet opening and a fluid outlet opening;
   a feed line supplying the fluid from said fluid outlet port of said reservoir to said fluid inlet opening of said plurality of permeameters;
   a plurality of permeameter isolation valves placed in said feed line wherein each said permeameter isolation valve controls the supply of fluid to one said permeameter; and
   means for measuring the amount of fluid passing through the core specimen in each said permeameter;
   wherein each said permeameter isolation valve includes an independent control permitting a permeability test in one of said plurality of permeameters to be independently started or finished irrespective of ongoing permeability tests in other said permeameters.

* * * * *